United States Patent [19]

Tomita et al.

[11] 4,187,429
[45] Feb. 5, 1980

[54] SCANNING APPARATUS FOR CROSS-SECTIONAL INSPECTION EQUIPMENT

[75] Inventors: Chuji Tomita, Tokyo; Hiroshi Abe, Kashiwa, both of Japan

[73] Assignee: Hitachi Medical Corporation, Tokyo, Japan

[21] Appl. No.: 906,278

[22] Filed: May 15, 1978

[30] Foreign Application Priority Data

May 13, 1977 [JP] Japan .................................. 52/55006
May 13, 1977 [JP] Japan .................................. 52/55007

[51] Int. Cl.² .............................................. A61B 6/00
[52] U.S. Cl. ................................. 250/445 T; 250/490
[58] Field of Search ........................... 250/445 T, 490

[56] References Cited

U.S. PATENT DOCUMENTS 3,999,073 12/1976 Hounsfield et al. .............. 250/445 T
4,104,527 8/1978 Tomita et al. .................... 250/445 T

*Primary Examiner*—Alfred E. Smith
*Assistant Examiner*—T. N. Grigsby
*Attorney, Agent, or Firm*—Wenderoth, Lind & Ponack

[57] ABSTRACT

A scanning apparatus for cross-sectional inspection equipment comprising a rotatable disc supporting an X-ray source and a detector. The rotation of this disc is quickly braked as a coil spring provided on a speed accelerating and reducing means is compressed. The start of rotation of this disc rapidly gains the required rotation speed by the recovering force of the same compressed coil spring. A cable extending from various devices including the X-ray source and the detector provided on the rotatable disc is releasably wound around a hollow drum provided on this disc. The rotation force produced in the rotatable disc by this cable is off-set by a rotation force applied in an opposite direction to this disc.

13 Claims, 7 Drawing Figures

SCANNING APPARATUS FOR CROSS-SECTIONAL INSPECTION EQUIPMENT

BACKGROUND OF THE INVENTION (a) Field of the Invention

The present invention relates to a scanning apparatus for use in a cross-sectional inspection unit, and more particularly it relates to scanning apparatus of the type described above arranged so as to be operative that a required cross section of an object to be inspected is scanned in various different directions by X-ray, and that the absorption information of X-ray obtained during the scanning is inputted in a computer, and that the cross-sectional image obtained as the result of computation is displayed on a surface such as a Braun tube.

(b) Description of the Prior Art

A scanning apparatus arranged so that a rotatable disc supporting an X-ray source and a detector is subjected to only rotational movement is known. In such known scanning apparatus, the rotatable disc is required to be rotated at a constant speed through the measurement interval which corresponds to the period of time in which X-ray emission continues and in which X-ray having passed through the object to be inspected is being received by the detector. In the past, it has been the usual way of accomplishing this requirement by preliminarily subjecting the rotatable disc to rotation before the starting of inspection by X-ray, and, at the end of inspection, by subjecting the rotating disc to gradual braking. In view of the fact, however, that the rotatable disc of this type has a very great weight of its own, and in view of the requirement that this disc carries thereon an X-ray source and a detector or other equipment which have to be kept from impact, the pre-inspection rotation period and the braking period tend to be quite lengthy.

On the other hand, an inspection of the object by X-ray requires that the rotatable disc be rotated through a substantial distance or angle or time. This, in turn, makes difficult the handling of the cable which extends from various kinds of equipment mounted on the rotatable disc and is led out to the outside of the scanning apparatus. In order to meet this requirement, it has been proposed in the past that the cable is given a substantial length of play so that the cable may be allowed to be fed out freely progressively as the disc rotates. This, however, still involves the risks that the cable could be bent forcibly or otherwise damaged during its feed and rewinding. Another known proposal is that the cable is adapted to be wound around a bobbin which is provided on the rotatable disc. This known arrangement still is entrained by a risk that the constant movement of the disc is hampered during the rewinding of the cable around the bobbin.

SUMMARY OF THE INVENTION

It is, therefore, a primary object of the present invention to provide a scanning apparatus which insures the rotatable disc which supports an X-ray source and a detector thereon to make a smooth and constant rotational movement.

Another object of the present invention is to provide a scanning apparatus of the type described, which allows the rotatable disc to make quick and smooth start of rotation and to make a smooth and rapid change in the direction of rotation and to make quick and smooth stop of rotation.

Still another object of the present invention is to provide a scanning apparatus of the type described, which insures that the cable extending from various equipment including an X-ray source and a detector mounted on the rotatable disc and being led out to the outside of the apparatus never interferes with the rotation of the rotatable disc.

These and other objects as well as the features and the advantages of the present invention will become apparent from the following detailed description of the invention when taken in conjunction with the accompanying drawings.

DETAILED DESCRIPTION OF THE PREFERRED EMBODIMENTS

Figure 1:
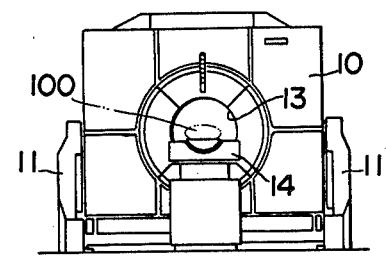
FIG. 1 is a diagrammatic front view of the scanning apparatus of the present invention.
Figure 2:
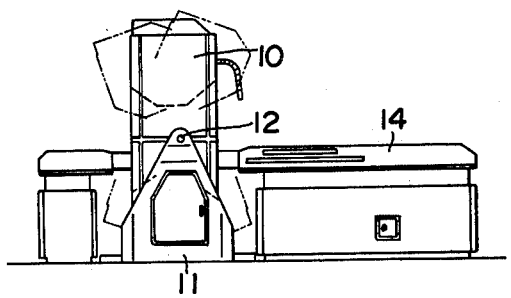
FIG. 2 is a diagrammatic view taken on the left side of the apparatus of FIG. 1.

As shown in FIGS. 1 and 2, the scanning apparatus of the present invention comprises a scanning mechanism section 10. This scanning mechanism section 10 is pivotably supported on a column extending from a base pedestal 11. This scanning mechanism section 10 is capable of being tilted about a horizontal axis 12 by being driven from an electric motor provided on the base pedestal 11. Also, the scanning mechanism section 10 is adapted to be brought into halt at any arbitrary angle. The scanning mechanism section 10 is provided with a receiving-opening 13 through which a patient's bed 14 is adapted to pass.

Figure 3:
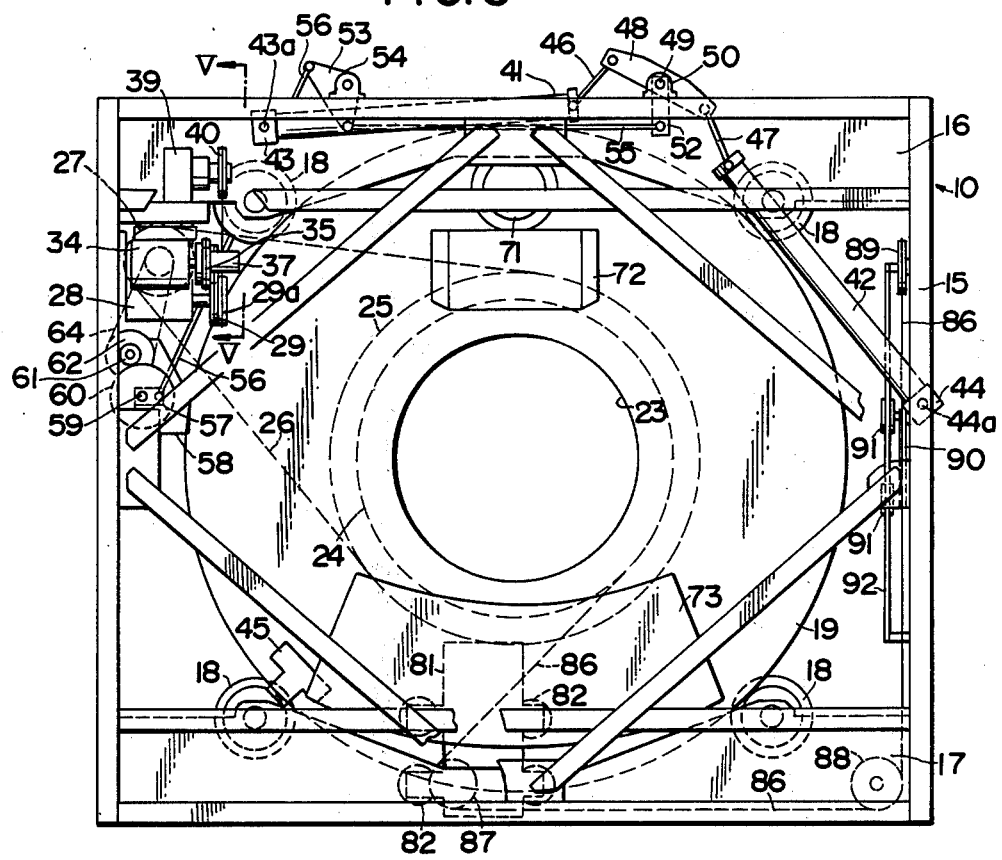
FIG. 3 is a diagrammatic front view of the scanning mechanism section in the scanning apparatus, with the outer panel being removed.
Figure 4:
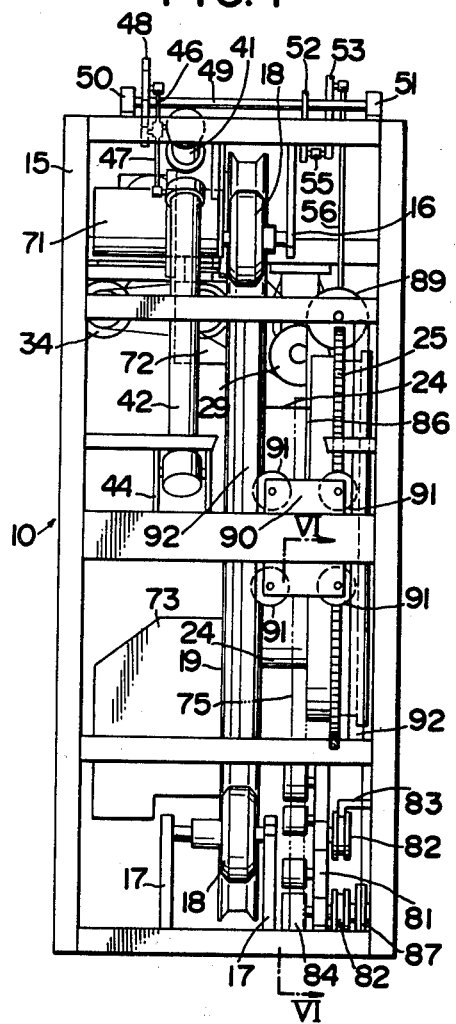
FIG. 4 is a diagrammatic view taken on the right side of the scanning mechanism section, with the outer panel being removed.

The scanning mechanism section 10 is provided with a frame 15 which is assembled with angular members and plate members as shown in FIGS. 3 and 4. In the drawings, an outer panel which is fixed to the frame 15 is omitted for clarity's sake. In the upper portion of the frame 15, there is provided a supporting plate 16 integrally therewith, and in the lower portion of the frame 15 is provided another supporting plate 17 integrally therewith. These supporting plates each is comprised of two plate members which are arranged at a distance therebetween. Rollers 18 are received between each pair of these supporting plates 16 and 17. The shafts of these rollers 18 are rotatably supported by bearings mounted on the respective supporting plates 16 and 17. A rotatable disc 19 is supported at its circumferential surface for rotation on these rollers. A recess having a substantially V-shaped cross section is formed on the circumferential surface of this rotatable disc 19. Each roller 18 has a surface which is snugly received in said circumferential recess of the rotatable disc 19.

Figure 5:
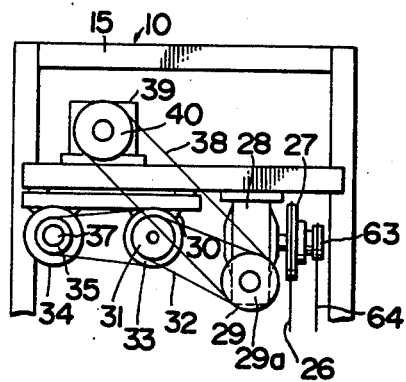
FIG. 5 is a diagrammatic sectional view of a part of the scanning mechanism section taken along the line V—V in FIG. 3.

A through-hole 23 is formed through the central portion of the rotatable disc 19. A hollow drum 24 is fixed to the rear side of the rotatable disc 19 at such position as to be located around the inner peripheral edge of the throughhole 23 of the disc 19. In the vicinity of the end portion of this hollow drum 24, there is fixed a sprocket wheel 25. This sprocket wheel 25 is connected to a sprocket 27 by means of a chain 26. As is well seen in FIG. 5, the sprocket 27 is fixed to an output shaft of a speed reducing means 28. A belt wheel 29 is fixed to an input shaft of the speed reducing means 28. This belt wheel 29 is connected by a belt to a belt wheel 31 of an electric motor 30. Furthermore, on the rotation shaft of the electric motor 30 is provided a belt wheel 33 coaxially with said belt wheel 31. This belt wheel 33, in turn, is connected by a belt to a belt wheel 35 of another electric motor 34. This belt wheel 35 is arranged so that it is arbitrarily connected to and disconnected from the electric motor 34 by an electromagnet clutch 37. This electromagnet clutch 37 is arranged to be operative to act so that, when the electric motor 30 is rotated, it disengages the belt wheel 35 from the electric motor 34, and also that, when the other electric motor 30 is connected to a power source, it acts to connect the belt wheel 35 to the electric motor 34. These two electric motors 30 and 34 have different capacities so that the rotatable disc 19 is rotated at different rotation speeds to obtain scanning at different scanning speeds. Also, on the input axis of the speed reducing means is provided a belt wheel 29a coaxially with the belt wheel 29. This belt wheel 29a is connected by a belt 38 to a belt wheel 40 which is provided on an electromagnet brake 39. This belt wheel 40 is connected to the electromagnetic brake 39 via a one-way clutch. Owing to these one-way clutch and electromagnetic brake, the belt wheel 40 is allowed to make unidirectional rotation when the electromagnetic brake 39 is in its braking state, and is allowed to make bi-directional rotations when the electromagnetic brake is in the non-braking state. It should be understood that the two electric motors 30 and 34 are fixed to a sub-frame which, in turn, is provided on the frame 15 via a buffer means. The electromagnetic brake 39 and the speed reducing means 28 are both provided directly on the frame 15.

Two speed accelerating and reducing means 41 and 42 are arranged in the vicinity of the circumferential edge of the rotatable disc 19. A striker 45 is fixed to a site on the circumferential edge of the rotatable disc 19. The two speed accelerating and reducing means 41 and 42 are arranged so as to be operative that, as the rotatable disc 19 is rotated in a certain direction, one of these two speed accelerating and reducing means 41 and 42 is moved to a position at which it is brought into engagement with the striker 45, and that, as the rotatable disc 19 is rotated in a direction opposite thereto, the other one of the means 41 and 42 is brought into engagement with the striker 45. To this end, the speed accelerating and reducing means 41 is pivotably supported at its one end by a shaft 43a on a bracket 43 which is mounted on the frame 15. The other speed accelerating and reducing means 42 is pivotably supported at its one end by a shaft 44a on a bracket 44 which is also mounted on the frame 15. To the other ends of these speed accelerating and reducing means 41 and 42 are pivotably coupled one end of rods 46 and 47, respectively. The other ends of these rods 46 and 47 are pivotably attached to an arm 48. This arm 48 has a shaft 49 at an intermediate site between the positions at which the other ends of these two rods 46 and 47 are attached to the arm 48. This shaft 49 is held by bearings 50 and 51 which are provided in the upper portion of the frame 15. A lever 52 is fixed to this shaft 49. Another arm 53 is pivotably supported by a bearing 54 in the upper portion of the frame 15. A rod 55 couples the lever 52 to the arm 53. Another rod 56 is coupled at one end to the arm 53. The other end of this rod 56 is coupled to a crank arm 57. This crank arm 57 is fixed to a shaft 59 which, in turn, is rotatably supported on a sub-frame 58 which is fixed to the frame 15. This shaft 59 is provided with a toothed wheel 60 which engages a toothed wheel 61 which is also carried on the subframe 58. A sprocket 62 is provided in coaxial relation with said toothed wheel 61. This sprocket 62 is connected by a chain 64 to a driving system for rotating the rotatable disc 19, i.e. connected to a sprocket 63 which is provided in coaxial relation with the sprocket 27 of the speed reducing means 28 shown in FIG. 5.

The rotation of the electric motor 33 or 34 is transmitted to the speed reducing means 28. The sprocket 27 which is mounted on the output shaft of the speed reducing means 28 causes the rotatable disc 19 to rotate. Along therewith, the sprocket 63 causes the crank arm 57 to rotate. As the rotatable disc 19 is rotated counterclockwise in FIG. 3, the crank arm 57 is rotated clockwise, so that the rod 56 moves downwardly to rotate the arm 54 to rotate counter-clockwise. Whereupon, the rod 55 is moved to the right side, and along therewith the arm 48 is rotated counterclockwise, and the speed accelerating and reducing means 41 is pivoted clockwise about the shaft 43a to a position at which it is brought into contact with the striker 45. Along therewith, the speed accelerating and reducing means 42 is pivoted clockwise about the shaft 44a to be brought into a position at which it is not in contact with the striker 45. Also, as the rotatable disc 19 is rotated clockwise in FIG. 3, the speed accelerating and reducing means 41 is moved to a position at which it is not brought into contact with the striker 45, whereas the speed accelerating and reducing means 42 is moved to a position at which it is brought into contact with the striker 45.

Figure 7:
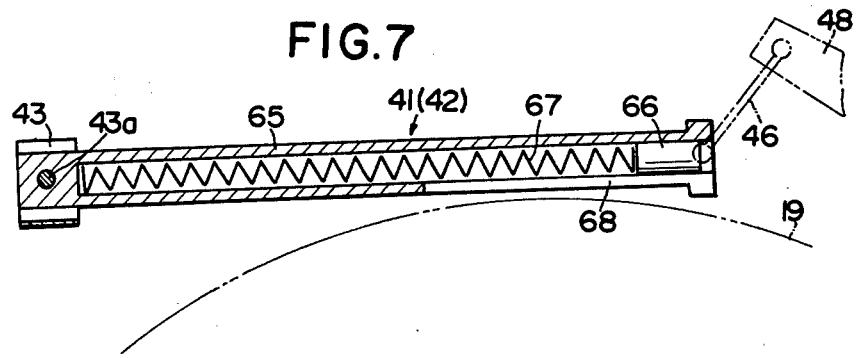
FIG. 7 is a diagrammatic sectional view of a speed accelerating and reducing means mounted on the scanning mechanism section.

Each of the speed accelerating and reducing means 41 and 42 has a hollow cylinder 65 whose one end is closed, as shown in FIG. 7. At a site near the open end of the cylinder 65, there is received a slide 66 within this cylinder 65. A coil spring 67 is arranged between the slide 66 and the closed end of the cylinder 65. Near the opening of the cylinder 65, there is formed a groove 68 in the cylinder 65 for receiving a part of the striker 45. Each of these speed accelerating and reducing means 41 and 42 is suspended at its open end side by rods 46 or 47, and the closed side thereof is supported by a bracket 43 or 44. Owing to the rotation of the rotatable disc 19, a part of the striker 45 is received in the groove 68 of the cylinder 65 and is brought into contact with the slide 66 to move the latter, to thereby compress the coil spring 67. On the other hand, the recovering force of this coil spring 67 causes the striker 45 to be pushed in the opposite direction by the slide 66. As will be described in detail later, the rotatable disc 19 is rapidly braked of its rotation by the compression of the coil spring 67, and also the disc 19 is quickly accelerated in its rotation speed by the application of the recovering force of the compressed coil spring 67.

An X-ray source is comprised of an X-ray tube 71 and a collimeter 72 which is provided at the X-ray exit of the X-ray tube 71. X-ray is given a certain diversion in a plane and is made into the so-called fan beam having no substantial thickness. A detector 73 is comprised of a known device, and has a number of elements covering said diversion of the X-ray. It should be noted that the X-ray source and the detector are so arranged on the rotatable disc 19 in such a way that the aforesaid plane in which is contained the X-ray will always contain the center axis 12 of the tilting of the scanning mechanism.

A cable connecting the X-ray tube and a high voltage generating means and a cable connecting the detector and an image processing means are not mentioned in the drawings. These cables are bundled together with other cables or wires of other equipment mounted on the rotatable disc 19, and the bundle of cable is led to the outside of the scanninhg apparatus. In the drawings, the bundle of cable comprising these cables and wires is generally indicated at 75 and is shown by a chain line.

Next, the operation of the scanning apparatus will be explained. An object 100 to be inspected, i.e. a patient, is mounted on a bed 14, and is placed through the receiving-opening 13 of the scanning mechanism section 10. The bed 14 carrying a patient thereon is moved so that the required cross section to be scanned of the patient is brought into agreement with the aforesaid plane in which is contained X-ray. Also, the scanning mechanism as a whole is tilted as required. As the electric motor 30 is rotated, the electromagnetic brake 39 is rendered to its non-braking state. The rotation of the electric motor 30 causes the sprocket 27 of the speed reducing means 28 to rotate via the belt wheel 31 and the belt 32. Whereupon, the rotatable disc 19 is caused to rotate counterclockwise in FIG. 3 on the rollers 18 from the chain 26 and the sprocket 25. In accordance with the rotation of the rotatable disc 19, the speed accelerating and reducing means 41 is rotated clockwise about the shaft 43a. As the striker 45 begins to compress the coil spring of the speed accelerating and reducing means 41, the electric motor 30 is brought to a halt temporarily. When the coil spring has been compressed completely, the striker 45 is pushed in the opposite direction owing to the recovering force of the coil spring. While the recovering force of the coil spring is still present, the electric motor 30 is started to rotate in the reverse direction. Thus, the rotatable disc 19 is rotated clockwise in FIG. 3. The rotatable disc 19 quickly gains the required speed of rotation by the action of the speed accelerating and reducing means and by the drive force of the electric motor, and is caused to rotate at a constant speed. As the rotatable disc 19 makes a revolution up to a predetermined position in the constant motion region, the high voltage generating means energizes the X-ray tube 71 to cause the latter to emit X-ray. At the end of a complete revolution of the rotatable disc 19 through 360 degrees, the X-ray tube ceases the emission of X-ray. During the emission of X-ray, the X-ray which has passed through the patient 100 is detected by the detector 73.

As the rotatable disc 19 is rotated for one complete revolution in the manner as stated above, the speed accelerating and reducing means 41 is pivoted counterclockwise about the shaft 43a and is thus moved to a non-engagement position with the striker 45. At the same time therewith, the speed accelerating and reducing means 42 is pivoted counterclockwise about the shaft 44a, and is thus moved to a position at which it engages the striker 45. The striker 45, then, is brought into contact with the slide 66 of the speed accelerating and reducing means 42 and pushes the coil spring, so that the electric motor 30 is cut off from the power source in the midway of compression of the coil spring. The rotatable disc 19, on the other hand, is quickly subjected to the braking force owing to the compression of the coil spring. Again, owing to the recovering force of the coil spring of the speed accelerating and reducing means 42, the striker 45 is then pushed in the opposite direction. And, by the recovering force alone of the coil spring, or during the period in which the recovering force of the coil spring is still working, the electric motor 30 is started, and the rotatable disc 19 is caused to rotate in the reverse direction. When the rotatable disc 19 is rotated in the reverse direction up to the starting position, the rotating disc 19 is brought to a halt either by the electromagnetic brake 39 alone or by the cut off of power to this electromagnetic brake 39.

In case it is intended to cause the rotatable disc 19 to make a constant movement but at a different speed, the electromagnetic clutch 37 is connected to a power source, and at the same time therewith the electric motor 30 is cut off from the power source, and the rotation of the electric motor 34 is transmitted to the belt wheel 31 via the belt wheels 35 and 33 and the belt. It should be understood that the capacity of the electric motor 34 may be set to be lower than that of the electric motor 30, so that the final revolution of the rotating disc 19 in the reverse direction which is caused by the electric motor 30 as stated previously may be caused by the electric motor 34.

Also, in the scanning apparatus of the present invention, arrangement may be provided so that the rotatable disc 19 is started of its rotation in the state that the coil spring of one of the speed accelerating and reducing means 41 and 42, for example the coil spring of the speed accelerating and reducing means 41, is compressed by the striker 45, and that the rotatable disc 19 is caused to make a reverse rotation as the coil spring of the other speed accelerating and reducing means 42 is compressed by the striker 45 and as the recovering force of this compressed coil spring is imparted to the rotatable disc 19, and finally that, again, in the state that the coil spring of the speed accelerating and reducing means 41 is compressed, the rotatable disc 19 is brought to a halt. Such mode of operation will be described hereunder. As the electric motor 30 is plunged into motion, and as the electromagnetic brake 39 is connected to the power source and is rendered to its non-braking state, the strike 45 is pushed as it receives the recovering force of the coil spring of the speed accelerating and reducing means 41, so that the rotatable disc 19 is rotated clockwise, and quickly gains the required speed of rotation and makes a constant movement. After the rotatable disc 19 has been thus rendered to making a constant speed rotation, X-ray is caused to emit, and this emission of X-ray is ceased at the time that this disc 19 has completed its one whole revolution at a constant speed through the angle of 360 degrees. At this point, the striker 45 compresses the coil spring of the speed accelerating and reducing means 42, and the rotatable disc 19 is quickly subjected to braking. On the other hand, as the striker 45 begins the compression of the coil spring of the speed accelerating and reducing means 42, the electric motor 30 is cut off from the power source, and is caused to make a reverse rotation. This reverse rotation of the electric motor 30 is carried out during the period of time when the striker 45 is still receiving the recovering force of the coil spring of the speed accelerating and reducing means 42. Whereby, the rotatable disc 19 is rotated counter-clockwise. Thus, the rotatable disc 19 is rotated through substantially one whole revolution, and the striker 45 again compresses the coil spring of the speed accelerating and reducing means 41, and as a result the rotatable disc 19 is quickly subjected to braking. When the striker 45 beings to compress the coil spring, the electric motor 30 is cut off from the power source, and when the striker 45 compresses the coil spring, the supply of power to the electromagnetic brake 39 is cut off and this latter is plunged into its braking state. Thus, the rotatable disc 19 is brought to a halt in the state that it has compressed the coil spring of the speed accelerating and reducing means 41. The one-way clutch of the electromagnetic brake 39 need to be constructed so that, at such time, it prohibits the rotatable disc 19 from making a rotation in the direction of rotation induced by the recovering force of the compressed coil spring.

As stated above, the scanning apparatus of the present invention is arranged so that its rotatable disc 19 is able to make more than one whole revolution. Therefore, the cable extending from the equipment including the X-ray source and the detector which are mounted on the rotatable disc 19 requires to be guided to be fed out or rewound without causing any deformation and without sustaining any damage and without interfering with the smooth rotation of the rotatable disc 19. The guiding means of this cable can employ various types of devices. However, the scanning apparatus according to the present invention is equipped with a novel guide means which can satisfy all of the above-said requirements. Description will hereunder be made with respect to the guide means employed in the present invention.

Figure 6:
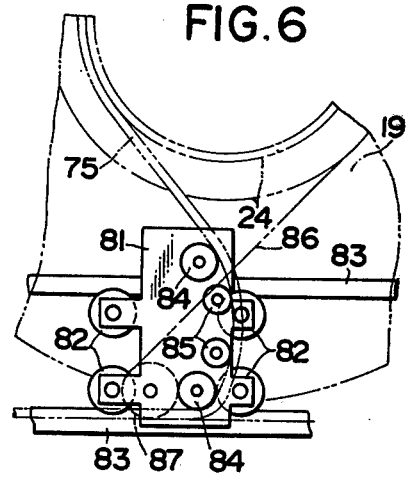
FIG. 6 is a diagrammatic sectional view of a part of the scanning mechanism section taken along the line VI—VI in FIG. 4.

On the rear side of the frame 11 of the scanning mechanism 10 is provided a guide panel 81. As is seen well in FIG. 6, there are rotatably mounted four rollers 82 on this guide panel. On this frame 11 are secured guide rails 83. The rollers 82 rotatably secured to the guide panel 81 engage the guide rails 83. The guide panel 81 is arranged so that it is allowed to move freely along the guide rails 83. Further rollers 84 and 85 are rotatably mounted on the guide panel 81. The cable 75 extending from the equipment mounted on the rotatable disc 19 is releasably wound around the drum 24 of the rotatable disc 19, or it is brought into contact with a portion of the drum 24, and this cable 75 is further brought into contact with the rollers 84 and 85 which are rotatably secured to the guide panel 81. This cable 75 is given a substantial length of play, and is connected to an image processing device including a computer and to a high voltage generating device all of which constitute a cross-sectional inspection unit together with the scanning apparatus. An end of either a wire or a rope 86 is fixed to this drum 24, and this wire or rope 86 is releasably wound around the drum 24 in a direction opposite to that in which the cable 75 is wound around the drum 24. The wire 86 is changed of its direction of winding or feed by a sheave 87 which is rotatably provided on the guide panel 81, and is guided by sheaves 88 and 89 which are rotatably secured to the frame 11, and the other end of the wire 86 is connected to a weight plate 90 which is provided on the side surface of the frame 11. Rollers 91 are rotatably secured on this weight plate 90. These respective rollers 91 engage the guide rail 92 which is provided on the side surface of the frame 11.

As the rotatable disc 19 is rotated counter-clockwise as stated previously, the cable 75 is fed out from the drum 24. Since, however, the guide panel 81 is caused to move to the right side in the drawing by the weight plate 90 via the sheave 87 and the rope 86, the cable 75 can be tensioned irrespective of the rotation of the rotatable disc 19. And, as the rotatable disc 19 is rotated clockwise as stated previously, the cable 75 is wound progressively around the drum 24, and the guide panel 81 is moved to the left side in the drawings. However, owing to the action of the weight plate 90, the cable 75 can be tensioned. At such time, the wire 86 is wound progressively around the drum 24 in a direction opposite to that of the cable 75 being wound around the drum 24. Accordingly, the torque of winding the cable 75 by the drum 24 can be off-set by the torque exerted by the wire 86 to rotate the drum 24 by the cooperation of the weight plate 90. Whereby, it is possible to cause a smooth rotation of the rotatable disc 19 at a constant speed.

What is claimed is:
1. A scanning apparatus, comprising:
a frame;
rollers rotatably secured on said frame;
a rotatable disc supported at its circumferential surface by said rollers;
a hollow drum provided in the vicinity of the rotation axis of said rotatable disc for the insertion therethrough of an object to be inspected;
an X-ray source and a detector arranged in positions opposed to each other with said drum intervening therebetween;
drive means for rotating said rotatable disc in a forward direction and in a reverse direction;
a striker provided on the rotatable disc;
two speed accelerating and reducing means movable alternately to a first position for engagement with said striker and to a second position for non-engagement with said striker; and
synchronizing means for bringing one of said two speed accelerating and reducing means to said first position in association with the forward rotation of said rotatable disc and for bringing the other one of said two speed accelerating and reducing means to said first position in association with the reverse rotation of said rotatable disc,
whereby said respective speed accelerating and reducing means are brought into engagement with said striker to perform braking the rotation and acceleration of speed of rotation of said rotatable disc.

2. A scanning apparatus according to claim 1, in which: said speed accelerating and reducing means each comprises: a hollow cylinder having an open end, a slide received in the vicinity of said open end of the cylinder and is adapted to be contacted by said striker, and a coil spring provided between said slide and said cylinder.

3. A scanning apparatus according to claim 2, in which: said drive means is arranged to be operative so that, after it has driven the rotatable disc to rotate in the forward direction, it drives this disc in the reverse direction, and thereafter it again drives the disc to rotate in the forward direction, and said synchronizing means is arranged to be operative so that it moves one of the two speed accelerating and reducing means to the first position during the forward rotation of said rotatable disc, and moves the other one of the speed accelerating and reducing means to the first position during the reverse rotation of said rotatable disc.

4. A scanning apparatus according to claim 2, in which: said drive means is arranged to be operative so that, after it has driven the rotatable disc to rotate in the forward direction from a certain position, it drives the disc again in the reverse direction to bring it back to said position, and said synchronizing means brings, at said position of the rotatable disc, one of said speed accelerating and reducing means to said first position, and brings the other one of the speed accelerating and reducing means to said first position during the reverse rotation of the disc.

5. A scanning apparatus according to claim 3, in which: said synchronizing means comprises: a first arm pivotably supported on the frame, rods coupled to the two speed accelerating and reducing means, respectively, at both sides of the pivotal axis of said first arm, a lever capable of pivoting through a same angle as that for said first arm, a second arm pivotably secured to said frame, a rod coupling said second arm to said lever, a crank arm provided on said frame and rotated by said drive means, and a rod coupling said crank arm to said second arm, and in which: said speed accelerating and reducing means are pivotably supported, at their other ends, on the frame.

6. A scanning apparatus according to claim 5, in which: said drive means comprises: an electric motor, a speed reducing means having an input shaft driven from said electric motor, and an electromagnetic brake coupled to the output shaft of said speed reducing means, and is arranged so that when said drum of the rotatable disc is driven for rotation by said output shaft of said speed reducing means, and when said electromagnetic brake is normally in its braking state and when said electric motor is actuated, said drive means is rendered to its non-braked state, and in which: said crank arm is rotated by the output shaft of said speed reducing means.

7. A scanning apparatus according to claim 4, in which: said synchronizing means comprises: a first arm pivotably supported on said frame, rods coupled to the two speed accelerating and reducing means, respectively, with the pivoting axis of said first arm intervening therebetween, a lever pivotable through a same angle as that of said first arm, a second arm pivotably supported on said frame, a rod coupling said second arm to said lever, a crank arm mounted on said frame and rotated by said drive means, and a rod coupling said crank arm to said second arm, and in which: said speed accelerating and reducing means are pivotably supported, at their other ends, on said frame.

8. A scanning apparatus according to claim 4, in which: said drive means comprises: a first electric motor, a speed reducing means having an input shaft driven from said first electric motor, and an electromagnetic brake having a one-way clutch connected to an output shaft of said speed reducing means, and said drive means is arranged so that it is rendered to be in its non-braked state when said electromagnetic brake is normally in its braking state and when said first electric motor is actuated, and that, in this non-braked state of this drive means, said one-way clutch thereof prohibits said rotatable disc from making a rotation from said position, whereas said output shaft of the speed reducing means rotates said crank arm.

9. A scanning apparatus according to claim 6 or claim 7, in which: said drive means further comprises a second electric motor having a capacity different from that of said first electric motor and being connected to said first electric motor via an electromagnetic clutch which is arranged so that this clutch is rendered to its non-engaging state during the rotation of said first electric motor.

10. A scanning apparatus, comprising:
a frame;
rollers rotatably secured to said frame;
a rotatable disc supported at its circumferential surface on said rollers;
a hollow drum provided in the vicinity of the rotation axis of said rotatable disc for the insertion therethrough of an object to be inspected;
an X-ray source and a detector which are mounted on said rotatable disc in positions opposed to each other with said drum intervening therebetween;
drive means for driving said rotatable disc to make at least one whole revolution; and
guide means for guiding a cable extending from equipment including said X-ray source and said detector which are mounted on said rotatable disc, said guide means comprising:
a guide panel movably mounted on said frame;
a weight plate movably mounted on said frame; and
a rope having one end fixed to said drum and releasably wound around this drum and having the other end connected to said weight plate and engaged with said guide panel so as to allow said weight plate to move said guide panel in a certain direction,
said cable being releasably wound around said drum in a direction opposite to that in which said rope is wound therearound and being engaged with said guide panel and being led out to the outside of the apparatus.

11. A scanning apparatus according to claim 10, in which: said guide panel has a plurality of rotatable rollers, and said cable is in contact with the circumferential surfaces of these respective rollers.

12. A scanning apparatus, comprising:
a frame;
rollers mounted on said frame;
a rotatable disc supported at its circumferential surface on said rollers;
a hollow drum provided in the vicinity of the rotation axis of said rotatable disc for the insertion therethrough of an object to be inspected;
an X-ray source and a detector which are mounted on said rotatable disc in positions opposed to each other with said drum intervening therebetween;
drive means for driving said rotatable disc to make at least one whole revolution and for driving said rotatable disc to rotate in a forward direction and in a reverse direction;
a striker mounted on said rotatable disc;
two speed accelerating and reducing means movable alternately to a first position for engagement with said striker and to a second position for non-engagement with said striker; and
synchronizing means for bringing one of said two speed accelerating and reducing means to said first position in association with the forward rotation of said rotatable disc and for bringing the other one of said two speed accelerating and reducing means to said first position in association with the reverse rotation of said rotatable disc,
there being provided an arrangement that said two speed accelerating and reducing means are brought into engagement with said striker to perform braking the rotation of and acceleration of speed of rotation of said rotatable, disc, said scanning apparatus further comprising guide means for guiding a cable extending from equipment including said X-ray source and said detector which are mounted on said rotatable disc, said guide means comprising:

a guide panel movably mounted on said frame;

a weight plate movably mounted in said frame; and a rope having one end fixed to said drum and releasably wound around this drum and having the other end connected to said weight plate and engaged with said guide panel so as to allow said weight plate to move said guide panel in a certain direction, said cable being releasably wound around said drum in a direction opposite to that in which said rope is wound therearound and being engaged with said guide panel and being led out to the outside of the apparatus.

13. A scanning apparatus according to claim 12, in which: said frame is tiltably supported on a base pedestal.

* * * * *